US007803961B2

(12) United States Patent
Vic Fernandez

(10) Patent No.: US 7,803,961 B2
(45) Date of Patent: Sep. 28, 2010

(54) PROCESS FOR MANUFACTURING DIMETHYL CARBONATE

(75) Inventor: Ignacio Vic Fernandez, Madrid (ES)

(73) Assignee: Sabic Innovative Plastics IP B.V., Bergen op Zoom (NL)

( * ) Notice: Subject to any disclaimer, the term of this patent is extended or adjusted under 35 U.S.C. 154(b) by 219 days.

(21) Appl. No.: 12/032,385

(22) Filed: Feb. 15, 2008

(65) Prior Publication Data

US 2008/0200714 A1 Aug. 21, 2008

Related U.S. Application Data

(60) Provisional application No. 60/890,277, filed on Feb. 16, 2007.

(51) Int. Cl.
C07C 69/96 (2006.01)

(52) U.S. Cl. ..................................................... 558/277

(58) Field of Classification Search .................. 558/277
See application file for complete search history.

(56) References Cited

U.S. PATENT DOCUMENTS

| 3,803,201 | A | 4/1974 | Gilpin et al. |
| 5,210,268 | A | 5/1993 | Fukuoka et al. |
| 5,380,908 | A | 1/1995 | Murata et al. |
| 5,426,207 | A | 6/1995 | Harrison et al. |
| 5,523,451 | A | 6/1996 | Rechner et al. |
| 5,599,965 | A | 2/1997 | Kricsfalussy et al. |
| 5,872,275 | A | 2/1999 | Komiya et al. |
| 6,093,842 | A | 7/2000 | Oyevaar et al. |
| 6,197,918 | B1 | 3/2001 | Uno et al. |
| 6,262,210 | B1 | 7/2001 | Tojo et al. |
| 6,315,868 | B1 | 11/2001 | Nisoli et al. |
| 6,392,078 | B1 | 5/2002 | Ryu et al. |
| 7,151,189 | B2 * | 12/2006 | Murthy et al. ............... 558/270 |
| 2001/0021786 | A1 | 9/2001 | Bruin et al. |
| 2007/0191623 | A1 | 8/2007 | Fukuoka et al. |
| 2007/0197814 | A1 | 8/2007 | Van Der Heide et al. |
| 2007/0197815 | A1 | 8/2007 | Van Der Heide et al. |
| 2007/0197816 | A1 | 8/2007 | Van Der Heide et al. |
| 2007/0219387 | A1 | 9/2007 | Fukuoka et al. |
| 2007/0255069 | A1 | 11/2007 | Fukuoka et al. |
| 2007/0260083 | A1 | 11/2007 | Fukuoka et al. |
| 2007/0260084 | A1 | 11/2007 | Fukuoka et al. |
| 2007/0260095 | A1 | 11/2007 | Fukuoka et al. |
| 2007/0265461 | A1 | 11/2007 | Fukuoka et al. |
| 2007/0270604 | A1 | 11/2007 | Fukuoka et al. |

FOREIGN PATENT DOCUMENTS

| CN | 1210850 | 3/1999 |
| CN | 1212172 | 3/1999 |
| CN | 1271721 | 11/2000 |
| EP | 0000894 A1 | 3/1979 |
| EP | 0001780 A1 | 5/1979 |
| EP | 0581115 | 2/1994 |
| EP | 0781760 A1 | 7/1997 |
| EP | 1156028 A1 | 11/2001 |
| EP | 1762559 A1 | 3/2007 |
| EP | 1783112 A1 | 5/2007 |
| EP | 1787976 A1 | 5/2007 |
| EP | 1792890 A1 | 6/2007 |
| EP | 1795522 A1 | 6/2007 |
| EP | 1795523 A1 | 6/2007 |
| GB | 1470160 | 4/1977 |
| JP | 63205101 | 8/1988 |
| JP | 05221929 | 8/1993 |
| JP | 06145113 | 5/1994 |
| JP | 06145114 | 5/1994 |
| JP | 06184055 | 7/1994 |
| JP | 06228026 | 8/1994 |
| JP | 2000191594 | 7/2000 |
| JP | 2001064235 | 3/2001 |

OTHER PUBLICATIONS

Xiong et al., "Separation of binary methanol-dimethyl carbonate azeotrope", Journal: General Review written in Chinese (with English Abstract), (2002), pp. 26-28, vol. 21(1); Publisher: Huaxue Gongye Chubanshe, China.

Han et al., "Development in Separation of Dimethyl Carbonate-Methanol Azeotrope", Journal: Jiangsu Polytechnic University (with English Abstract), (2003), pp. 61-64, vol. 15, Part 4.

Wei et al., "Separation of dimethyl carbonate from methanol-dimethyl carbonate azeotrope", Taiyuan University of Technology, Taiyuan, Peoples Republic of China. Huagong Jinzhan, (2005), pp. 1234-1238, vol. 24(11).

Li, et al., "Study on extractive distillation of methanol and dimethyl carbonate azeotrope using furfural extractant", Department of Chemistry, Huazhong University of Science and Technology, (2000), pp. 12-13, vol. 28(4), Publisher: Huaxu Gongyebu Di-6 Shejiyuan.

Database WPI, Week 200137, Thomson Scientific, London, GB; AN 2001-347764; XP002487820 & JP 2001 064234 A (Chiyoda Corp); Mar. 13, 2001; abstract.

* cited by examiner

Primary Examiner—Rei-tsang Shiao
(74) Attorney, Agent, or Firm—Larson & Anderson, LLC

(57) ABSTRACT

A method of forming a dialkyl carbonate stream, includes obtaining a byproduct stream from a diaryl carbonate formation reaction that has alkanol, residual dialkyl carbonate, and residual aromatic compound. This byproduct stream is introduced to a distillation column to produce an alkanol tops stream and a first dialkyl carbonate bottoms stream. The alkanol tops stream is reacted with oxygen, carbon monoxide, and catalyst to form a second dialkyl carbonate stream that is introduced to the distillation column. The alkanol tops stream from the column contains alkanol, dialkyl carbonate, and less than 20 ppm aromatic compound. The first dialkyl carbonate bottoms stream from the column contains dialkyl carbonate, water, aromatic compound, and less than 2,000 ppm alkanol and is introduced to a water separation device to produce a product dialkyl carbonate stream and a water stream.

16 Claims, 4 Drawing Sheets

PROCESS FOR MANUFACTURING DIMETHYL CARBONATE

CROSS-REFERENCE TO RELATED APPLICATIONS

The present application claims priority from and is a nonprovisional application of U.S. Provisional Patent Application Ser. No. 60/890,277 filed on Feb. 16, 2007, which is incorporated herein by reference for all purposes.

BACKGROUND OF THE INVENTION

Diaryl carbonates, such as diphenyl carbonate, are an important reactant in the production of polycarbonate resins. As the uses to which polycarbonates are put have increased, the safe and efficient production of diaryl carbonates has become of greater significance. Early processes for the production of diaryl carbonates utilized phosgene as a reagent. The toxicity of phosgene, however, prompted the development of a non-phosgene process. The non-phosgene process is well-known in the art and is described in U.S. patent application Ser. Nos. 4,410,464, 5,344,954, 6,784,277, 7,141,641, and 7,288,668, which are incorporated herein by reference.

As shown schematically in FIG. 1, the non-phosgene process involves three reaction steps. First, a dialkyl carbonate (e.g. dimethyl carbonate) and water are formed by reacting an alkanol (e.g. methanol) with oxygen and carbon monoxide in the presence of a catalyst. The dialkyl carbonate is separated from water and residual reaction components including carbon monoxide, oxygen, and alkanol. In a second reaction step, the dialkyl carbonate reacts with an aromatic alcohol (e.g. phenol) to produce an arylalkyl carbonate (e.g. phenylmethyl carbonate) and an alkanol (e.g. methanol). Then, in the third reaction step, two molecules of an arylalkyl carbonate undergo a disproportionation reaction to produce one molecule of diaryl carbonate (e.g. diphenyl carbonate) and one molecule of dialkyl carbonate. The diaryl carbonate is separated from the byproducts and residual reaction components (i.e. phenol, methanol, and dimethyl carbonate) to produce a product diaryl carbonate stream.

To aid in the efficiency of producing diaryl carbonates, it would be useful to recycle the byproducts and residual reaction components (i.e. aromatic alcohol, alkanol, and dialkyl carbonate). Possible uses of these components include the reuse of the dialkyl carbonate in the formation reaction to produce diaryl carbonate. Furthermore, residual alkanol can be reacted to form/reform dialkyl carbonate.

Cost-efficient recycling of the byproduct stream has however proven to be difficult to achieve. Process instabilities occurring in the diaryl carbonate production facility lead to inconsistent chemicals and chemical concentrations in the byproduct line. For example, if there is a water leak (e.g. from heat transfer equipment) in the diaryl carbonate production facility, the byproduct line would contain water. Water in a dialkyl carbonate formation reactor hinders the formation reaction of alkanol into dialkyl carbonate. Furthermore, a water leak in the diaryl carbonate production facility may cause separation problems leading to an increase in byproducts and residual reaction components in the byproduct line. Diaryl carbonate formation reaction byproducts or residual reaction components including aromatic alcohol (e.g. phenol) and its aromatic ether byproduct (e.g. anisole) can lead to reactivity or separation problems or to the formation of chlorinated aromatics (e.g. di- and tri-chlorophenols and chloroanisols) which can degrade in separation equipment of a dialkyl carbonate plant and cause fouling in piping and process equipment. When this happens chlorophenols and chloroanisoles can be formed in the dialkyl carbonate reactors and can thermally decompose in later stages of the process forming a coke-type residue that can clog transfer lines, reactors, separation equipment, and heat transfer equipment.

A plant using a byproduct line from a diaryl carbonate formation reaction would be required to constantly determine what is present in the byproduct line, determine the concentration of its components, and determine a strategy for separating and using the desired components from the balance of the byproduct line. This has proven to be cost inefficient in that significant additional labor, energy, and equipment costs would be required to recycle the byproduct line. Due to this cost inefficiency and no matter what the good intentions of the company toward the environment are, the byproduct line and its contents are often discarded.

It would be extremely beneficial to find a process where the components in the byproduct line from the diaryl carbonate production plant could be efficiently recycled.

SUMMARY OF THE INVENTION

The present inventors have found a process where a byproduct line from a diaryl carbonate production plant can be efficiently recycled and its residual alkanol be used to form or reform dialkyl carbonate and its residual dialkyl carbonate may be separated and used in a later diaryl carbonate formation reaction. In one embodiment the present invention provides a method of forming a combined dialkyl carbonate stream using a byproduct stream from a diaryl carbonate formation reaction. The method comprises the steps of:

(1) obtaining a byproduct stream from a diaryl carbonate formation reaction that contacts dialkyl carbonate with aromatic alcohol to produce diaryl carbonate and alkanol, the byproduct stream comprising alkanol, dialkyl carbonate, and an aromatic compound, wherein the aromatic compound comprises aromatic alcohol, aromatic ether, or both aromatic alcohol and aromatic ether, (2) separating the byproduct stream to produce a first alkanol stream and a first dialkyl carbonate stream,
  wherein the first alkanol stream comprises alkanol, dialkyl carbonate, and less than 20ppm aromatic compound, and
  wherein the first dialkyl carbonate stream comprises dialkyl carbonate, alkanol, and aromatic compound, (3) contacting the first alkanol stream with oxygen and carbon monoxide in the presence of a catalyst, thereby creating a second dialkyl carbonate stream comprising dialkyl carbonate, alkanol, and water, (4) separating the second dialkyl carbonate stream to produce a second alkanol stream and a third dialkyl carbonate stream,
  wherein the second alkanol stream comprises alkanol and dialkyl carbonate, and
  wherein the third dialkyl carbonate stream comprises alkanol, dialkyl carbonate, and water, and (5) combining the first and third dialkyl carbonate streams to form a combined dialkyl carbonate stream comprising dialkyl carbonate, alkanol, water, and aromatic compound, thereby producing a combined dialkyl carbonate stream.

In another embodiment the present invention provides a method of forming a product dialkyl carbonate stream using a byproduct stream from a diaryl carbonate formation reaction, the method comprising the steps of:

(1) obtaining a byproduct stream from a diaryl carbonate formation reaction that contacts dialkyl carbonate with aromatic alcohol to produce diaryl carbonate and alkanol, the byproduct stream comprising alkanol, dialkyl carbonate, and an aromatic compound, wherein the aromatic compound comprises aromatic alcohol, aromatic ether, or both aromatic alcohol and aromatic ether, (2) introducing the byproduct stream to a distillation column to produce an alkanol tops stream and a first dialkyl carbonate bottoms stream, (3) contacting the alkanol tops stream with oxygen, carbon monoxide, and catalyst to form a second dialkyl carbonate stream comprising dialkyl carbonate, alkanol, and water, (4) introducing the second dialkyl carbonate stream to the same distillation column as in step (2),
wherein the alkanol tops stream comprises alkanol, dialkyl carbonate, and less than 20 ppm aromatic compound, and
wherein the first dialkyl carbonate bottoms stream comprises dialkyl carbonate, water, aromatic compound, and less than 2,000 ppm alkanol, and (5) introducing the first dialkyl carbonate bottoms stream to a water separation device to produce a product dialkyl carbonate stream and a water stream, thereby producing a product dialkyl carbonate stream.

DETAILED DESCRIPTION

The present inventors have found a process where a byproduct line from a diaryl carbonate production plant can be efficiently recycled and its alkanol used to form or reform dialkyl carbonate and its dialkyl carbonate separated and used in a later diaryl carbonate formation reaction. These byproducts and residual reaction components are removed from the diaryl carbonate production facility and are sent to a dialkyl carbonate production/recovery facility where dialkyl carbonate is separated and alkanol is reacted with oxygen and carbon monoxide in the presence of a catalyst to produce or reproduce dialkyl carbonate.

In the specification and the claims which follow, reference will be made to a number of terms which shall be defined to have the following meanings:

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

Suitable alkanols include primary, secondary, and tertiary $C_1$-$C_{12}$ alkanols, with primary $C_1$-$C_6$ alkanols being preferred. Highly preferred alkanols include methanol.

Figure 2:
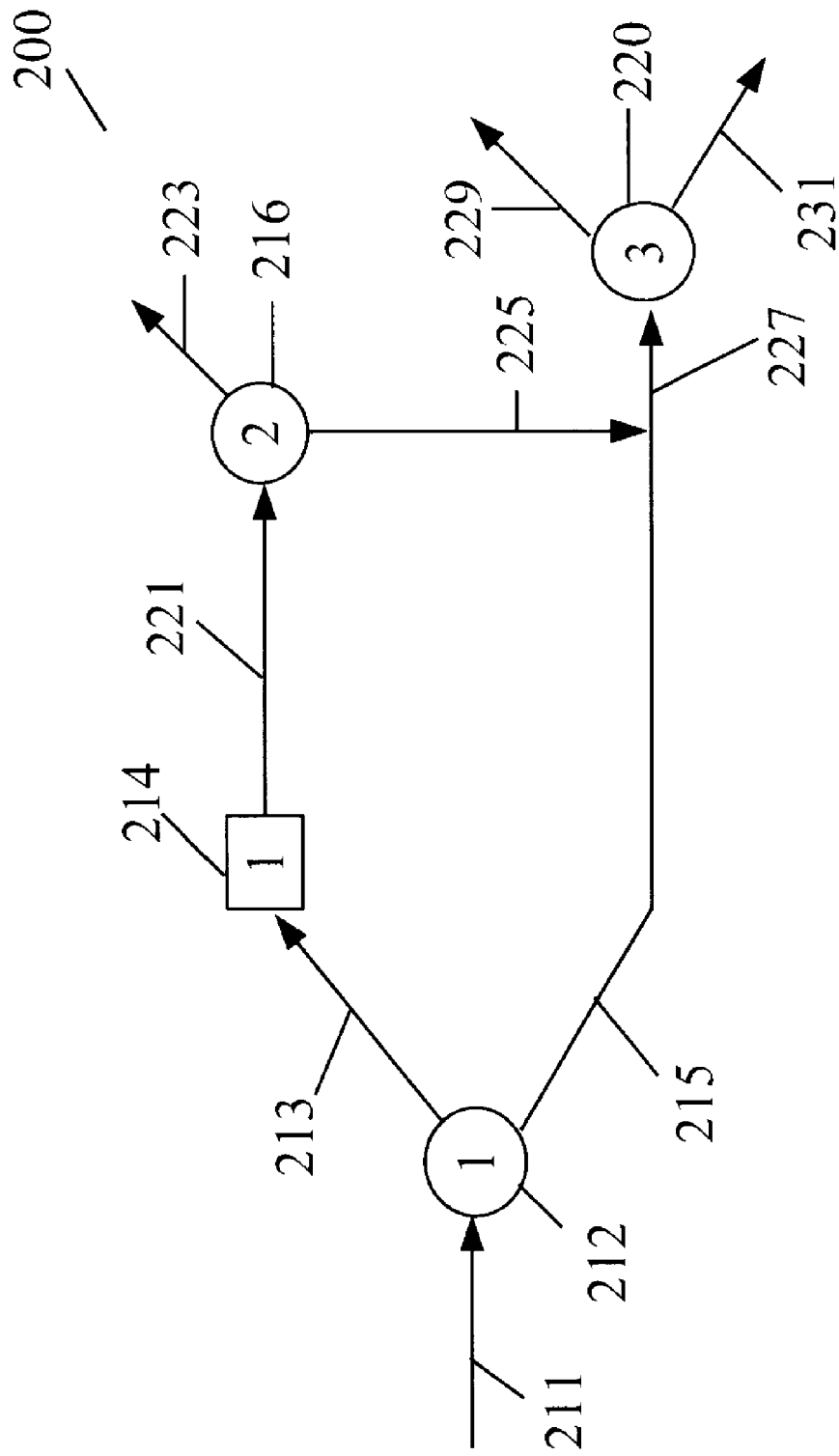
FIG. 2 is a schematic diagram showing an equipment configuration in a dialkyl carbonate production facility.

Suitable dialkyl carbonates are those that include a carbonate group disposed between two alkyl groups. The dialkyl carbonate formation reaction, such as that as depicted in FIG. 2, will create a dialkyl carbonate which is dependent upon the alkanol used as a reactant. If methanol is used as a reactant, the dialkyl carbonate will comprise dimethyl carbonate, which is a preferred dialkyl carbonate.

Suitable diaryl carbonates include those that are used to effect a transesterfication reaction between the free-hydroxy ends of dihydroxy compounds to form polycarbonate. Diaryl carbonates include a carbonate group disposed between two aryl groups. The diaryl carbonate formation reaction depicted in FIG. 1 will create a diaryl carbonate which is dependent upon the aromatic alcohol used as a reactant. If phenol is used as a reactant, the diaryl carbonate will comprise diphenyl carbonate, which is a preferred diaryl carbonate.

Figure 1:
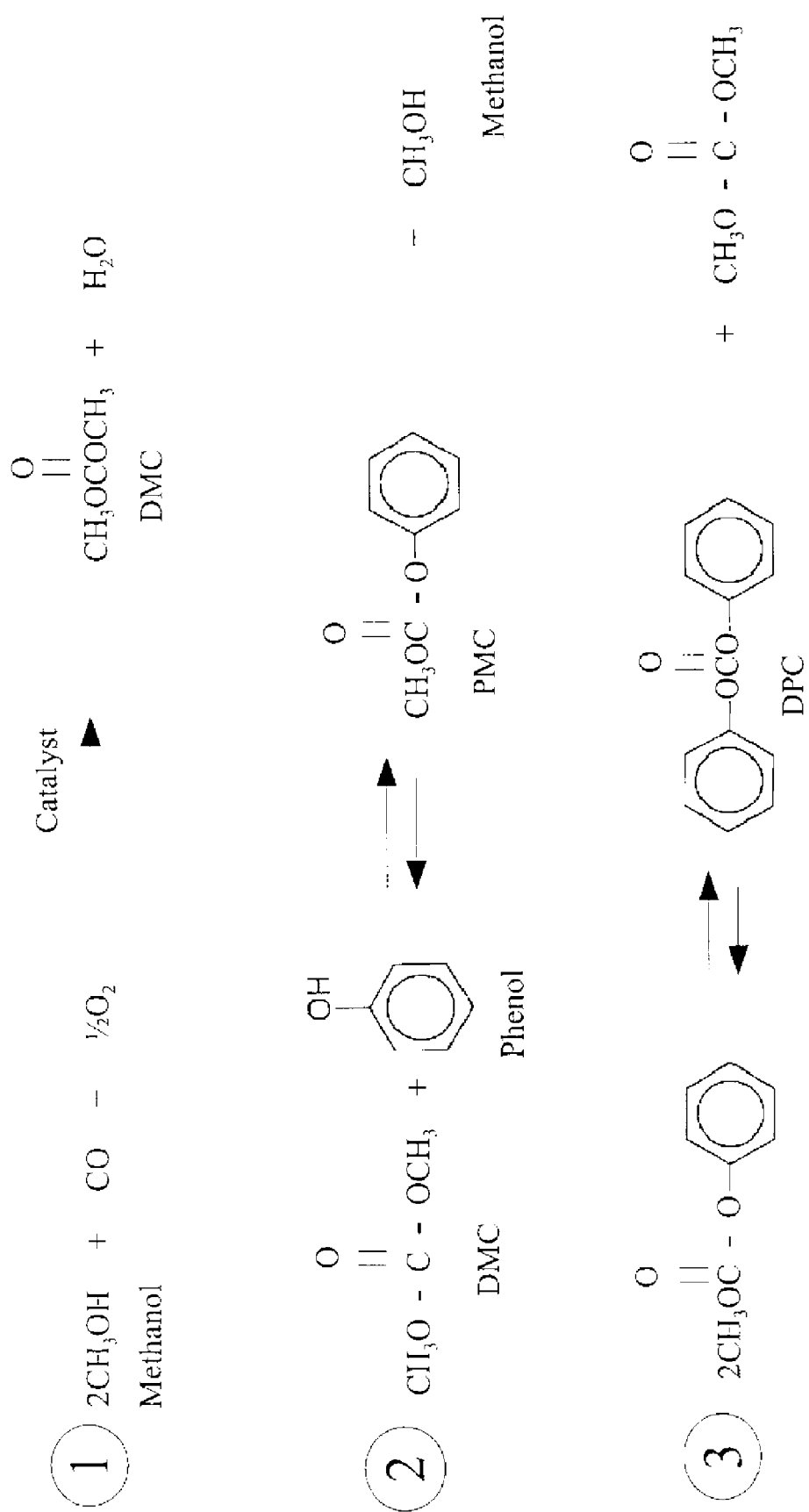
FIG. 1 is a reaction schematic diagram.

"Aromatic compound" present in streams of the present invention is dependent upon the diaryl carbonate produced in the diaryl carbonate production facility. As illustrated in FIG. 1, the diaryl carbonate produced will comprise components of both the aromatic alcohol and the dialkyl carbonate. Where the diaryl carbonate comprises diphenyl carbonate, the aromatic alcohol will comprise phenol, which is a preferred aromatic alcohol. Reaction byproducts of the "aromatic alcohol", such as an aromatic ether, for example anisole may also be present in the byproduct stream.

The Process:

In one embodiment the present invention provides a method of forming a combined dialkyl carbonate stream using a byproduct stream from a diaryl carbonate formation reaction. The method steps are illustrated with reference to FIG. 2. The method steps are preferably performed in a dialkyl carbonate production/recovery facility 200.

In this embodiment, a byproduct stream 211 is obtained or received from a diaryl carbonate formation reaction that contacts dialkyl carbonate with aromatic alcohol to produce diaryl carbonate and alkanol, the byproduct stream comprising alkanol, dialkyl carbonate, and aromatic compound. The aromatic compound comprises aromatic alcohol, its aromatic ether degradation product, or both aromatic alcohol and aromatic ether. These are common reactants and byproducts formed in the non-phosgene process used to produce diaryl carbonate, which is well-known in the art and is described in U.S. Pat. Nos. 4,410,464, 5,344,954, and 7,288,668 which are incorporated by reference.

As shown schematically in FIG. 1, in this process for making diaryl carbonate, a dialkyl carbonate (e.g. dimethyl carbonate, DMC) reacts with an aromatic alcohol (e.g. phenol) to produce an alkylaryl carbonate (e.g., phenylmethyl carbonate, PMC) and an alkanol (e.g. methanol). In a next step, two molecules of phenylmethyl carbonate undergo a disproportionation reaction to produce one molecule of diphenyl carbonate and one molecule of dimethyl carbonate. The diphenyl carbonate is then separated from the byproducts and residual reaction components (i.e. phenol, methanol, and dimethyl carbonate) to produce a product diphenyl carbonate stream. The byproducts and residual reaction components are removed from the diaryl carbonate production reaction as a byproduct stream 211. The byproducts and unreacted reactants are removed together or they are removed separately in later stages of the production process. As noted above, this byproduct stream 211 may further comprise water. In the present invention, this byproduct stream 211 is collected and sent to the dialkyl carbonate production/recover facility 200.

Looking again at FIG. 2, the byproduct stream 211 is separated in a first separation step to produce a first alkanol stream 213 and a first dialkyl carbonate stream 215. Separation steps in FIG. 2 are denoted with a circle and reaction steps are denoted with a square. In the first separation step in FIG. 2 the byproduct line 211 is treated to produce a dialkyl carbonate rich stream 215 containing aromatic compound and water if present in byproduct stream 211 and a stream 213 rich in alkanol. The alkanol rich stream 213 is reacted to increase the concentration of dialkyl carbonate in stream 221. Stream 221 is treated to produce a dialkyl carbonate rich stream 225 and an alkanol rich stream 223. The dialkyl carbonate rich stream 225 from the second separation step and the dialkyl carbonate rich stream 215 from the first separation step are combined to form stream 227.

Equipment 212 for accomplishing the first separation is not particularly limited and may be any known equipment for separation including the use of a distillation column or columns and/or flash vessels among other process equipment 212. However, it has been found that the combination of certain components of the byproduct stream 211 results in the formation of an azeotropic mixture and separation techniques related to the separation of components of azeotropic mixtures may be required. For example in one embodiment, the combination of dialkyl carbonate and alkanol can result in the formation of an azeotropic mixture. Therefore in this embodiment separation of these components from one another will require the use of known methods of azeotrope separation and/or distillation.

In a preferred embodiment, the separation step is performed such that the first alkanol stream 213 comprises alkanol, dialkyl carbonate and less than 20 ppm aromatic compound, and more preferably less than 10 ppm, for example less than 5 ppm, aromatic compound. It is also preferred that the first treatment step is performed such that the first dialkyl carbonate stream 215 comprises alkanol, dialkyl carbonate, aromatic compound, and water if present in byproduct line 211. As illustrated above, because of the azeotropic nature of these streams the first alkanol stream preferably comprises greater than 60 wt % alkanol (more preferably greater than 70 wt % alkanol), less than 40 wt % dialkyl carbonate (more preferably less than 30 wt %), and less than 20 ppm aromatic alcohol while the first dialkyl carbonate stream preferably contains less than 2,000 ppm alkanol (more preferably less than 1,000 ppm, for example less than 500 ppm, alkanol), greater than 60 wt % dialkyl carbonate (more preferably greater than 70 wt % dialkyl carbonate), aromatic alcohol, and water if present in byproduct stream 211.

Next, the first alkanol stream 213 is contacted with oxygen and carbon monoxide in the presence of a catalyst in a first reaction process, thereby creating a second dialkyl carbonate stream 221 comprising dialkyl carbonate, alkanol, and water. As described in U.S. Pat. Nos. 6,784,277 and 7,141,641, which are incorporated herein by reference, the present reaction preferably takes place in the presence of a copper chloride (CuCl) catalyst and hydrochloric acid. Thus the present reaction step 214 includes the removal of residual catalyst, oxygen, carbon monoxide, and hydrochloric acid from the reaction product to produce the second dialkyl carbonate stream. The removal of these components from the reaction product is preferably accomplished as described below and in U.S. Pat. No. 7,141,641. Where the formation reaction proceeds in the presence of a copper chloride catalyst and hydrochloric acid, the second dialkyl carbonate stream will comprises less than 5 ppm CuCl catalyst and less than 10 ppm hydrochloric acid.

The equipment 214 used to effect the reaction is not particularly limited. As described herein the reaction of alkanol with oxygen and carbon monoxide in the presence of a catalyst to produce dialkyl carbonate is well-known in the art and is described in U.S. Pat. Nos. 6,784,277 and 7,141,641, which are incorporated herein by reference. The reaction forms a second dialkyl carbonate stream 221 comprising formed dialkyl carbonate, unreacted alkanol, and formed water.

The second dialkyl carbonate stream 221 is separated in a second separation step to produce a second alkanol stream 223 and a third dialkyl carbonate stream 225. The equipment 216 used in the second separation step to accomplish this separation is not particularly limited and may be accomplished by known methods of separation including the use of a distillation column(s) and or flash vessels among others. However, as described above, it has been found that the combination of certain components of the second dialkyl carbonate stream 221 result in the formation of an azeotropic mixture and separation techniques related to the separation of components of azeotropic mixtures may be required. For example, as described above, the combination of dialkyl carbonate and alkanol may result in the formation of an azeotrope. Therefore in one embodiment separation of these components from one another will require the use of known methods of azeotrope separation and/or distillation.

In a preferred embodiment this separation step is performed such that the third dialkyl carbonate stream 225 comprises dialkyl carbonate, water, and less than 1,000 ppm alkanol (more preferably less than 500 ppm alkanol) while the second alkanol stream 223 comprises alkanol, dialkyl carbonate, and less than 20,000 ppm water. In a more preferred embodiment the second alkanol stream 223 comprises greater than 60 wt % alkanol, less than 40 wt % dialkyl carbonate, and less than 20,000 ppm water and most preferably greater than 70 or 80 wt % alkanol, less than 30 or 20 wt % dialkyl carbonate, and less than 10,000 ppm water (more preferably less than 5,000 ppm water). The second alkanol stream 223 is preferably introduced back to reactor 214 as a feedstock. The third dialkyl carbonate stream 225 preferably will comprise more than 60 wt % dialkyl carbonate, for example more than 70 wt % dialkyl carbonate, and water. In an optional embodiment, not depicted in FIG. 2, the third dialkyl carbonate stream 225 is treated to reduce the concentration of water prior to being combined with the first dialkyl carbonate stream 215 as described below.

Next, the first 215 and third 225 dialkyl carbonate streams are combined to form a combined dialkyl carbonate stream 227 comprising dialkyl carbonate, water, aromatic compound and alkanol. The combined dialkyl carbonate stream 227 preferably comprises less than 2,000 ppm alkanol, more preferably less than 1,500 ppm alkanol, and most preferably less than 1,000 ppm alkanol. This stream 227 may be further purified preferably as described below.

The combined dialkyl carbonate stream 227 comprises both dialkyl carbonate formed in the dialkyl carbonate production/recovery facility 200 as well as dialkyl carbonate originally contained in byproduct line 211. It also comprises water formed in the first reaction section 214 and water, if any, originally contained in byproduct line 211. The step of combining the first 215 and third 225 dialkyl carbonate streams forms a combined dialkyl carbonate stream 227. The equipment used to accomplish this step is not particularly limited. For example, the step may be accomplished by introducing both streams to a mix vessel and drawing off the combined dialkyl carbonate stream 227 from the vessel.

In a preferred embodiment also depicted in FIG. 2, the above described method further comprises a third separation step to separate the combined dialkyl carbonate stream 227 into a product dialkyl carbonate stream 229 and a water stream 231. The equipment 220 used in the third separation step to accomplish the product recovery is not particularly limited and may be accomplished using known methods of separation including the use of distillation columns and or flash vessels among others. In a preferred embodiment the separation equipment used in the third separation step 220 will comprise water separation equipment. In this preferred embodiment the combined dialkyl carbonate stream 227 is cooled in and/or before entering the water separation equipment and water separation occurs to produce a product dialkyl carbonate organic phase and a water phase. When water separation equipment is used to effect a water separation the present inventors have found that the combined dialkyl carbonate stream 227 should comprise less than 2,000 ppm alkanol (e.g. less than 1,500 ppm or less than 1,000 ppm alkanol) to ensure quality separation of a dialkyl carbonate organic phase from the water phase. The organic dialkyl carbonate phase is separated from the water phase and removed as a product dialkyl carbonate stream 229. The product dialkyl carbonate stream 229 will comprise alkanol, dialkyl carbonate, aromatic compound, and preferably less than 200 ppm water (for example less than 100 ppm water). The water phase is removed from the water separation equipment as a water stream 231 that comprises water formed in reaction equipment 214 and water, if present, in the byproduct line 211. The water stream 231 may further comprise preferably less than 2,000 ppm dialkyl carbonate. Water stream 231 can then be sent to a waste water treatment facility for treatment and purification before being discarded.

As illustrated, the byproduct line 211 may further comprise water from the diaryl carbonate production facility. As indicated above, water contained in the byproduct line can be the result of a water leak (for example in heat exchange equipment) occurring in the diaryl carbonate production facility and is usually accompanied with an increase in aromatic alcohol in the byproduct line from the diaryl carbonate production facility. Water in dialkyl carbonate formation reaction equipment 214 hinders the formation reaction of the alkanol to dialkyl carbonate. When water is present in the byproduct line 211, separation process step 212 occurs such that the first dialkyl carbonate stream 215 further comprises the water contained in the byproduct line. The first dialkyl carbonate stream 215 further comprises water that was originally present in byproduct line 211 that is then combined with the third dialkyl carbonate line 225 that comprises water formed in reaction equipment 214 to form the combined dialkyl carbonate stream 227. Preferably the combined stream 227 is then separated as described above.

In another preferred embodiment, the second alkanol stream 223 may be combined with the byproduct line 211 and/or with first alkanol stream 213 prior to entering the reaction section 214, or they may be combined within reaction equipment 214. In this embodiment both the first 213 and the second 223 alkanol streams are contacted with oxygen and carbon monoxide in the presence of a catalyst to create the second dialkyl carbonate stream 221.

A "virgin" alkanol stream may also be combined with the first alkanol stream 213 prior to entering the reaction equipment 214 or within the reaction equipment 214 where they are reacted to form the second dialkyl carbonate stream 221 as described above. The term "virgin" is herein understood to mean an alkanol stream that is provided with a purity of greater than 99.95%.

Figure 3:
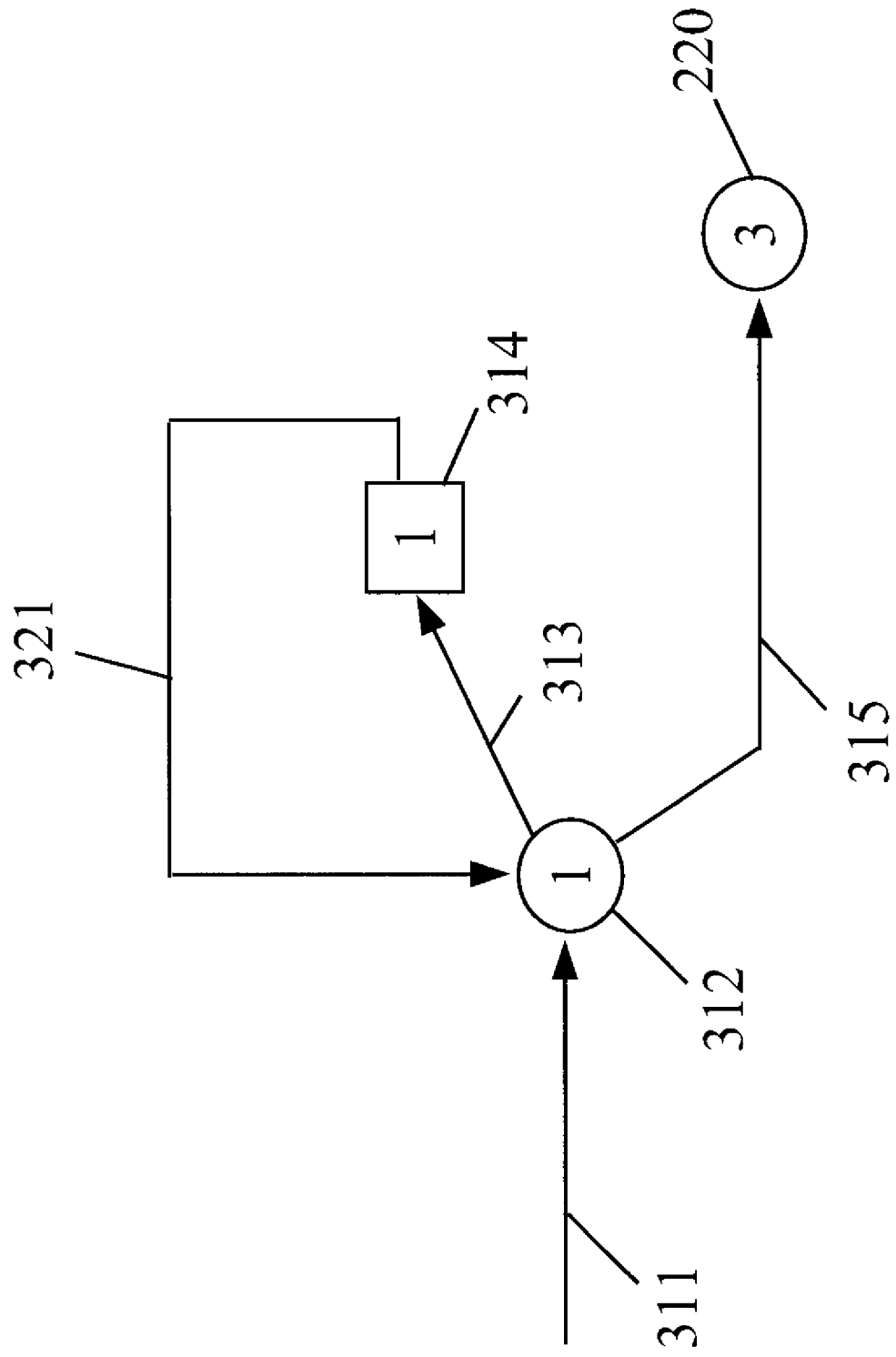
FIG. 3 is a schematic diagram showing an equipment configuration in a dialkyl carbonate production facility.

In a particularly preferred embodiment, the Inventors have found that the first and second separation steps 212, 216 can occur using a common distillation column preferably at overlapping times. In this embodiment, as shown in FIG. 3, byproduct line 311 is obtained from a diaryl carbonate production reaction as described herein. The byproduct stream 311 is introduced to a first distillation step, here distillation column 312. A first alkanol stream 313 is obtained as a tops product and a first dialkyl carbonate stream 315 is obtained as a bottoms product from the distillation column 312.

The first alkanol stream 313 is contacted with oxygen and carbon monoxide in the presence of a catalyst (and optionally hydrochloric acid as described above) in a first reaction step 314 to produce a second dialkyl carbonate stream 321 comprising dialkyl carbonate, alkanol, and water. As described above, the present reaction step 314 may further comprise the use of a copper chloride catalyst and hydrochloric acid that are removed with residual oxygen and carbon monoxide from the reaction product to produce the second dialkyl carbonate stream 321. The second dialkyl carbonate stream 321 is then introduced to the same distillation column 312.

Dialkyl carbonate and water present in the second dialkyl carbonate stream 321 are combined with dialkyl carbonate present, and any water present, in the byproduct stream 311 to form a first dialkyl carbonate stream 315. The first dialkyl carbonate stream 315 is removed as a bottoms product which may be further purified and separated as described above with regard to the third purification step 220.

Further to the present embodiment where the first and second separation steps are performed in a common distillation column, the present invention provides a method of forming a product dialkyl carbonate stream using a byproduct stream from a diaryl carbonate formation reaction, the method comprising the steps of:

(1) obtaining a byproduct stream from a diaryl carbonate formation reaction that contacts dialkyl carbonate with aromatic alcohol to produce diaryl carbonate and alkanol, the byproduct stream comprising alkanol, dialkyl carbonate, and an aromatic compound, wherein the aromatic compound comprises aromatic alcohol, aromatic ether, or both aromatic alcohol and aromatic ether, (2) introducing the byproduct stream to a distillation column to produce an alkanol tops stream and a first dialkyl carbonate bottoms stream, (3) contacting the alkanol tops stream with oxygen, carbon monoxide, and catalyst to form a second dialkyl carbonate stream comprising dialkyl carbonate, alkanol, and water, (4) introducing the second dialkyl carbonate stream to the same distillation column as in step (2), wherein the alkanol tops stream comprises alkanol, dialkyl carbonate, and less than 20 ppm aromatic compound, and wherein the first dialkyl carbonate bottoms stream comprises dialkyl carbonate, water, aromatic compound, and less than 2,000 ppm alkanol, and (5) introducing the first dialkyl carbonate bottoms stream to a water separation device to produce a product dialkyl carbonate stream and a water stream, thereby producing a product dialkyl carbonate stream.

By using a common distillation column, the present embodiment has the advantage of reducing the energy and equipment costs needed to treat the byproduct stream. By treating the byproduct stream and reaction product stream (the second dialkyl carbonate stream 321) in one distillation column at overlapping times, one is able to efficiently incorporate the ability to recycle the byproduct from a diaryl carbonate production facility into a dialkyl carbonate production facility.

The term "overlapping times" is herein understood to mean that at some point of operation the distillation column receives both the byproduct stream 311 and the second dialkyl carbonate stream 321 at the same time. Where the byproduct stream 311 has no flow the column 312 can receive the second dialkyl carbonate stream 321 by itself. When the second dialkyl carbonate stream 321 has no flow, the column 312 can receive the byproduct stream 311 by itself. When both stream 311, 321 have flow, the column 312 receives both at the same time.

Figure 4:
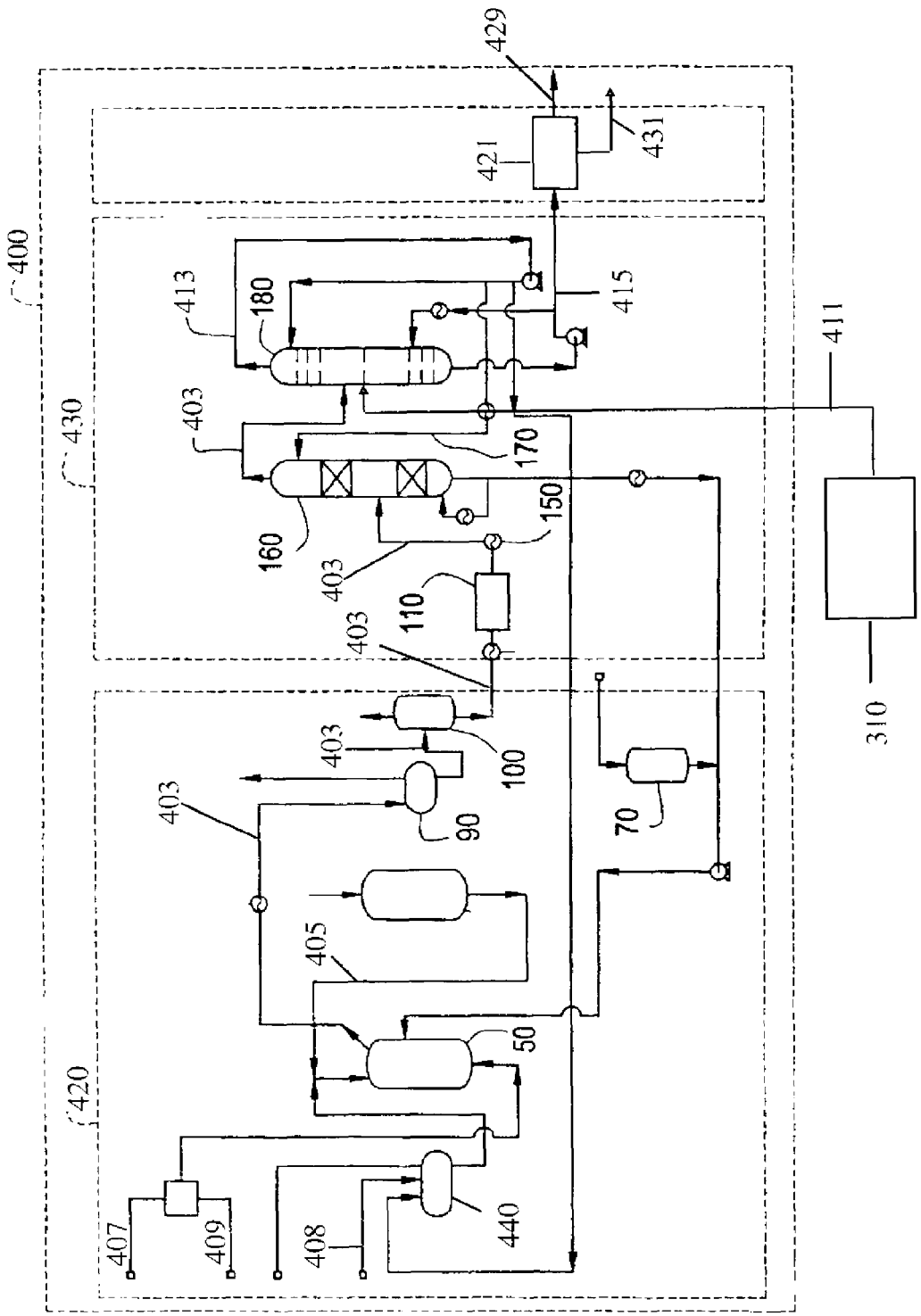
FIG. 4 is a schematic diagram showing an equipment configuration in a dialkyl carbonate production facility.

FIG. 4 illustrates a dialkyl carbonate production/recovery plant design 400 in accordance with a preferred embodiment of the present invention. The plant 400 has a reaction section 420 and a separation section 430. In a preferred embodiment, the methods used in the reaction section 420 and the separation section 430 to form the dialkyl carbonate are as described in U.S. Pat. No. 6,784,277, which is incorporated herein by reference. A byproduct line 411 is obtained from a diaryl carbonate formation plant 310 and introduced to azeotrope column 180. Azeotrope column 180 produces a first alkanol stream 413 tops product and a first dialkyl carbonate stream 415 bottoms product. The first alkanol tops stream is sent to alkanol storage tank 440 where it may be combined with a virgin alkanol stream 408.

The catalyzed reaction of the alkanol, oxygen 409, and carbon monoxide 407 may be performed in a single reactor 50, or in two or more reactors 50. The conditions for performing this step should be selected to maximize the yield of dialkyl carbonate while minimizing the degradation of dialkyl carbonate. Preferably, the reaction is performed in a single reactor 50, at a temperature of about 50° C. to about 250° C. and preferably at least about 100° C. for example up to about 150° C. The reactor 50 is preferably kept at a pressure of about 15 to about 35 bar gauge (bar) and preferably at least about 20 bar up to about 28 bar. In the case of dual reactor systems, the catalyst 405 may be recycled between tanks. The catalyst concentration should be sufficiently high to produce an acceptable yield, but should be kept below a concentration that would cause solid setting of the catalyst in the reactor 50 or clogging of the equipment. In this regard, the reaction equipment configurations including the gas and liquid flow schemes outlined in copending PCT Patent Application Serial No. PCT/IB2008/050570 filed on Feb. 15, 2008 and copending U.S. patent application Ser. No. 12/032,149 filed on Feb. 15, 2008 which are incorporated herein by reference, should be employed.

Oxygen 409 may be provided in any form, with gaseous forms being preferred. Suitable oxygen 409 sources include, for example, air, and oxygen-containing gases having at least about 95 weight percent molecular oxygen, preferably at least about 99 weight percent molecular oxygen. Carbon monoxide 407 is preferably supplied as a gas having at least about 90 weight percent, preferably at least about 95 weight percent, more preferably at least about 99 weight percent, carbon monoxide.

The reactants including the first alkanol stream 413, oxygen 409, and carbon monoxide 407 are preferably added in a molar ratio of (about 0.5 to about 0.7):(about 0.04 to about 0.06):(about 0.8 to about 1.2), respectively. A highly preferred molar ratio of alkanol:oxygen:carbon monoxide is (about 0.6):(about 0.05):(about 1).

Suitable catalyst 405 include those comprising iron, copper, nickel, cobalt, zinc, ruthenium, rhodium, palladium, silver, cadmium, rhenium, osmium, iridium, platinum, gold, mercury, and the like, and combinations comprising at least one of the foregoing metals. Preferred catalysts may comprise copper. A highly preferred catalyst comprises copper and chloride ion in a molar ratio of about 0.5 to about 1.5. Within this range, a molar ratio of at least about 0.8 may be preferred. Also within this range, a molar ratio of up to about 1.2 may be preferred. Highly preferred catalysts include cuprous chloride (CuCl) and cupric chloride ($CuCl_2$), with cuprous chloride being more highly preferred. During operation of the process, a suitable chloride ion concentration may be maintained by the addition of hydrochloric acid (HCl).

The amount of catalyst 405 used relative to the reactants will depend on the identity of the catalyst. For example, when the catalyst comprises CuCl, a highly preferred catalyst concentration is about 140 to about 180 grams per liter of reaction mixture. During operation, the catalyst may initially be added from a catalyst tank. Sufficient HCl is preferably added to reactor 50 from a hydrochloric acid tank 70 during the course of the reaction to maintain a molar ratio of Cu:Cl close to 1.0. The concentration of HCl is preferably continuously determined and controlled by the addition of HCl. A typical mass ratio for HCl feed to total liquid feed is about $6 \times 10^{-4}$ to about $8 \times 10^{-4}$.

The reaction produces a second dialkyl carbonate stream 403 comprising a dialkyl carbonate, an alkyl chloroformate, hydrochloric acid, water, carbon dioxide, and carbon monoxide, residual alkanol, and oxygen, as well as side-products such as alkyl chlorides and dialkyl ethers. The second dialkyl carbonate stream 403 is typically withdrawn from the reactor 50 in a gas/vapor form. The term "vapor" is meant to refer to gaseous organic components of the mixture such as, for example, evaporated dialkyl carbonates, alcohols, alkyl chloroformates, etc., and to water vapor. That is, the term "vapor" refers to fluids having a boiling point of at least −50° C. at one atmosphere. In contrast, the term "gas" is meant to refer to the gaseous oxygen, carbon dioxide, carbon monoxide, and optional nitrogen. That is, the term "gas" refers to fluids having a boiling point less than −50° C. at one atmosphere. The vapor may be at least partially condensed in a condenser, and fed to a first gas-liquid separator 90. The apparatus may optionally employ a single gas-liquid separator, or a plurality of (i.e., at least 2; preferably up to about 5) gas-liquid separators. The first gas-liquid separator 90 may be kept at a pressure within about 10%, more preferably within about 1%, of the pressure of the reactor 50. The gas effluent from the first gas-liquid separator 90 may be recycled, for example to reuse excess carbon monoxide. The second dialkyl carbonate stream 403 may be sent to a second gas-liquid separator 100, which preferably has a pressure less than about 20% of the pressure of the reactor 50 (e.g., preferably less than 3 bar gauge, more preferably about 0.2 bar gauge) to preferably achieve separation of at least about 90%, more preferably at least 95%, by weight of the remaining gas in the second dialkyl carbonate stream 403. In a highly preferred embodiment, substantially all of the gas is removed from the second dialkyl carbonate stream 403. The gas effluent removed from the second gas-liquid separator 100 can also be recycled. It is preferred that the vapor in the second dialkyl carbonate stream 403 be in a partially condensed form (i.e., at least about 10% condensed), more preferably a fully condensed form (i.e., at least about 90% condensed), before entering the first gas-liquid separator 90, and between the first gas-liquid separator 90 and the second gas-liquid separator 100.

The second dialkyl carbonate stream 403 exiting the second gas-liquid separator 100 may be in a single liquid phase. After the second gas-liquid separator 100, the second dialkyl carbonate stream 403 may proceed through a fluid passageway 110 that removes alkyl chloroformate from the stream 403. U.S. Pat. No. 6,784,277, which is incorporated herein by reference, describes benefits and methods of removing alkyl chloroformate from the mixture using fluid passageway 110.

After exiting the fluid passageway 110, the second dialkyl carbonate stream 403 may, optionally, pass through a second heat exchanger 150 to at least partially vaporize the stream 403. This second heat exchanger 150 may have a residence time of less than 10 minutes. This vaporization step may also be accomplished without a heat exchanger by lowering the pressure applied to the condensed stream 403 (e.g., by passing the condensate into an acid removal column 160 that is kept at a relatively lower pressure). The vaporized second dialkyl carbonate stream 403 may then, optionally, be treated to remove HCl, preferably by injecting it into an acid removal column 160. The acid removal column 160 may also help remove any entrained catalyst (e.g., CuCl) that could otherwise contribute to downstream corrosion. In the acid removal column 160, the vaporized condensate may preferably encounter a counter-flowing liquid supplied by counter-flowing liquid line 170 to a higher point in the column (e.g., the upper third). The counter-flowing liquid may trap the remaining HCl and other reactants, which may be removed from the bottom of the acid removal column 160 and recycled to the reactor 50.

The second dialkyl carbonate mixture 403 is removed from the top of the acid column 160 and passed into the azeotrope distillation column 180, described above. A byproduct stream 411 comprising alkanol, dialkyl carbonate, and aromatic alcohol is obtained from a diaryl carbonate production facility and is also passed to the azeotrope column. The azeotrope column 180 produces a first alkanol tops stream 413 that is then sent to an alkanol storage vessel 440. The first dialkyl carbonate stream 415 is removed as a bottoms product from column 180.

The alkanol stream 413 from azeotrope column 180 is in line with the above specifications and is still suitable for use in the dialkyl carbonate formation reaction section 420. The first dialkyl carbonate bottoms stream 415 from the azeotrope column 180 is in line with the specification described above and comprises water and dialkyl carbonate that is both formed in the reaction section 420 and dialkyl carbonate that is transferred to the facility from the diacyl carbonate production facility via byproduct stream 411. The first dialkyl carbonate stream 415 also contains residual aromatic alcohol from the diaryl carbonate production facility and water, if present, in recycle line 411.

The first dialkyl carbonate stream 415 removed as a bottoms product from column 180 and is then sent to a further purification/separation device 421. Purification/separation device 421 is preferably a water separation device as described above, that separates a dialkyl carbonate phase from a water phase thereby producing a product dialkyl carbonate stream 429 and a water stream 431.

EXAMPLES

Having described the invention in detail, the following examples are provided. The examples should not be considered as limiting the scope of the invention, but merely as illustrative and representative thereof.

Illustration 1:

A computer simulation using Aspen Simulation software was run to determine the product stream component concentration on streams from an azeotrope distillation column having 60 theoretical trays. Six runs were performed using six different feed stream compositions from a proposed diaryl carbonate production facility. These feed stream configurations are indicated in Table 1. The azeotrope distillation column was set to run throughout the six runs according to the following additional parameters:

Top Product Stream: 28 wt % (maximum) dimethyl carbonate (DMC) and 1 ppm (maximum) aromatic alcohol.
Top Condenser Reflux Ratio (L/D): 1.35.
First feed stream: 53,956 Kg/hr (50.96 wt % MeOH, 41.40 wt % DMC, 3.78 wt % water, the balance includes reaction byproducts such as methyl chloride, methylal and dimethyl ether)
Second feed stream (byproduct from diaryl carbonate production plant): 6,375 Kg/hr
Bottom Product Stream: 150 ppm (maximum) methanol Table 2 illustrates the calculated component results of the top and bottom streams from the azeotrope column. As illustrated in table 2 anisole and phenol will be removed from the azeotrope column in the bottom product stream, together with water and DMC. Further, the data contained in Table 2 demonstrates that very little to no aromatic compounds will be present in the top product stream from the azeotrope column ensuring that the azeotrope feed to the DMC reactor(s) contains little to no aromatic impurities.

TABLE 1

(Flow rate in Kg/hr)

| | Flowrate | Composition % wt | | | | Flowrate | Composition % wt | | | Flowrate |
|---|---|---|---|---|---|---|---|---|---|---|---|
| Run | From DMC | Methanol | DMC | Water | Others | From DPC | Methanol | DMC | Anisole | Phenol | Total |
| 1 | 54000 | 51.0 | 41.4 | 3.8 | 3.9 | 6375 | 72.4 | 26.6 | — | — | 60375 |
| 2 | 54000 | 51.0 | 41.4 | 3.8 | 3.9 | 6439 | 71.7 | 26.3 | — | 1 | 60439 |
| 3 | 54000 | 51.0 | 41.4 | 3.8 | 3.9 | 6711 | 68.8 | 25.3 | — | 5 | 60711 |
| 4 | 54000 | 51.0 | 41.4 | 3.8 | 3.9 | 6439 | 71.7 | 26.3 | 1 | — | 60439 |
| 5 | 54000 | 51.0 | 41.4 | 3.8 | 3.9 | 6711 | 68.8 | 25.3 | 5 | — | 60711 |
| 6 | 54000 | 51.0 | 41.4 | 3.8 | 3.9 | 6711 | 68.8 | 25.3 | 25 | 25 | 60711 |

TABLE 2

| | Impurities in azeotrope recycled from DPC Plant | | Product composition from Azeotrope column in DMC plant | | | | | | | | | |
|---|---|---|---|---|---|---|---|---|---|---|---|---|
| | | | TOP STREAM | | | | | BOTTOM STREAM | | | | |
| | PheOH % | Anisole % | Phenol | Anisole | DMC | Methanol | Water | Phenol | Anisole | DMC | Methanol | Water |
| Run 1 | 0 | 0 | 0.0% | 0.0% | 28.0% | 67.7% | 0.2% | 0.0% | 0.0% | 84.9% | 0.4% | 14.7% |
| Run 2 | 1 | 0 | 0.0% | 0.0% | 28.0% | 67.7% | 0.2% | 0.0% | 0.6% | 84.3% | 0.4% | 14.6% |
| Run 3 | 5 | 0 | 0.0% | 0.0% | 28.0% | 67.7% | 0.2% | 0.0% | 3.2% | 82.2% | 0.4% | 14.3% |
| Run 4 | 0 | 1 | 0.0% | 0.0% | 28.0% | 67.7% | 0.2% | 0.6% | 0.0% | 84.3% | 0.4% | 14.6% |
| Run 5 | 0 | 5 | 0.0% | 0.0% | 28.0% | 67.7% | 0.2% | 3.2% | 0.0% | 82.2% | 0.4% | 14.3% |
| Run 6 | 2.5 | 2.5 | 0.0% | 0.0% | 28.0% | 67.7% | 0.2% | 1.6% | 1.6% | 82.2% | 0.4% | 14.3% |

Illustration 2:

In a second illustration, test results are provided that demonstrate the affect of aromatic compounds (phenol and anisole) on DMC/water separation in the decanter/water separator downstream of the azeotrope column in a DMC plant.

Experiment 1

A mixture comprising 16.5 ml water, 83.5 ml DMC, and 0.015 ml methanol was prepared and introduced to a flask at 60° C. Also introduced to the flask was 1 gr of phenol and 1 gr of anisole. The flask was sealed and the mixture was stirred for five minutes and cooled to room temperature. The mixture separated into two phases (aqueous and organic) and component concentrations of each phase was analyzed by gas chromatography (GC) and are reported in Tables 3 and 4.

Experiment 2

A mixture comprising 16.5 ml water, 83.5 ml DMC, 0.015 ml methanol was prepared and introduced to a flask at 60° C. Also introduced to the flask was 5 gr of phenol and 5 gr of anisole. The flask was sealed and the mixture was stirred for five minutes and cooled to room temperature. The mixture separated into two phases (aqueous and organic) and component concentrations of each phase was analyzed by GC and are reported in Tables 3 and 4.

Experiments 1 and 2 demonstrate that anisole and phenol impurities remain largely in the organic phase while only small amounts are contained in the aqueous phase. Furthermore, the presence of anisole and/or phenol up to 5 wt % in the bottom stream from azeotrope column in a DMC plant will not impair water separation in the decanter/water separator downstream therefrom.

TABLE 3

| | Organic Phase (% weight on water free basis) | | | |
|---|---|---|---|---|
| | Methanol | DMC | Anisole | Phenol |
| Experiment 1 | 0.01 | 97.59 | 1.29 | 1.11 |
| Experiment 2 | 0.01 | 88.23 | 6.09 | 5.67 |

TABLE 4

| | Aqueous Phase (% weight, water by balance) | | | |
|---|---|---|---|---|
| | Methanol | DMC | Anisole | Phenol |
| Experiment 1 | 0.68 | 9.70 | <0.01 | 0.04 |
| Experiment 2 | 0.08 | 9.52 | <0.01 | 0.20 |

The invention claimed is:

1. A method of forming a combined dialkyl carbonate stream using a byproduct stream from a diaryl carbonate formation reaction, the method comprising the steps of:
   (1) obtaining a byproduct stream from a diaryl carbonate formation reaction that contacts dialkyl carbonate with aromatic alcohol to produce diaryl carbonate and alkanol, the byproduct stream comprising alkanol, dialkyl carbonate, and an aromatic compound, wherein the aromatic compound comprises aromatic alcohol, aromatic ether, or both aromatic alcohol and aromatic ether,
   (2) separating the byproduct stream to produce a first alkanol stream and a first dialkyl carbonate stream,
      wherein the first alkanol stream comprises alkanol, dialkyl carbonate, and less than 20 ppm aromatic compound, and
      wherein the first dialkyl carbonate stream comprises dialkyl carbonate, alkanol, and aromatic compound,
   (3) contacting the first alkanol stream with oxygen and carbon monoxide in the presence of a catalyst, thereby creating a second dialkyl carbonate stream comprising dialkyl carbonate, alkanol, and water,
   (4) separating the second dialkyl carbonate stream to produce a second alkanol stream and a third dialkyl carbonate stream,
      wherein the second alkanol stream comprises alkanol and dialkyl carbonate, and
      wherein the third dialkyl carbonate stream comprises alkanol, dialkyl carbonate, and water, and
   (5) combining the first and third dialkyl carbonate streams to form a combined dialkyl carbonate stream comprising dialkyl carbonate, alkanol, water, and aromatic compound,
   thereby producing a combined dialkyl carbonate stream.

2. The method of claim 1, further comprising the step of combining the first and second alkanol streams and wherein in step (3) the first and second alkanol streams are contacted with oxygen and carbon monoxide in the presence of a catalyst to create the second dialkyl carbonate stream.

3. The method claim 2, further comprising the step of combining a virgin alkanol stream with the first and second alkanol streams and wherein in step (3) the virgin, the first, and the second alkanol streams are contacted with oxygen and carbon monoxide in the presence of a catalyst to create the second dialkyl carbonate stream.

4. The method of claim 2, wherein separating steps (2) and (4) are accomplished by distillation.

5. The method of 4, wherein steps (2) and (4) are performed in a common distillation column at overlapping times.

6. The method of claim 1, wherein:
   the first alkanol stream comprises greater than 60 wt % alkanol, less than 40 wt % dialkyl carbonate, and less than 10 ppm aromatic compound,
   the second alkanol stream comprises greater than 60 wt % alkanol and less than 40 wt % dialkyl carbonate,
   the combined dialkyl carbonate stream comprises dialkyl carbonate, water, aromatic compound, and less than less than 2,000 ppm alkanol.

7. The method of claim 6, further comprising the step of separating the combined dialkyl carbonate stream to produce a product dialkyl carbonate stream and a water stream.

8. The method of claim 1, wherein:
   the dialkyl carbonate comprises dimethylcarbonate, the alkanol comprises methanol, the diaryl carbonate comprises diphenyl carbonate, the aromatic alcohol comprises phenol, and the aromatic ether comprises anisole.

9. The method of claim 1, wherein the catalyst comprises CuCl, step (3) is performed in the presence of hydrochloric acid, and the second dialkyl carbonate stream further comprises oxygen, carbon monoxide, catalyst, and hydrochloric acid, and wherein the method further comprises a step performed after step (3) and before step (4) of treating the second dialkyl carbonate stream to reduce the concentration of oxygen, carbon monoxide, catalyst, and hydrochloric acid.

10. A method of forming a product dialkyl carbonate stream using a byproduct stream from a diaryl carbonate formation reaction, the method comprising the steps of:

(1) obtaining a byproduct stream from a diaryl carbonate formation reaction that contacts dialkyl carbonate with aromatic alcohol to produce diaryl carbonate and alkanol, the byproduct stream comprising alkanol, dialkyl carbonate, and an aromatic compound, wherein the aromatic compound comprises aromatic alcohol, aromatic ether, or both aromatic alcohol and aromatic ether, (2) introducing the byproduct stream to a distillation column to produce an alkanol tops stream and a first dialkyl carbonate bottoms stream, (3) contacting the alkanol tops stream with oxygen, carbon monoxide, and catalyst to form a second dialkyl carbonate stream comprising dialkyl carbonate, alkanol, and water, (4) introducing the second dialkyl carbonate stream to the same distillation column as in step (2), wherein the alkanol tops stream comprises alkanol, dialkyl carbonate, and less than 20 ppm aromatic compound, and wherein the first dialkyl carbonate bottoms stream comprises dialkyl carbonate, water, aromatic compound, and less than 2,000 ppm alkanol, and (5) introducing the first dialkyl carbonate bottoms stream to a water separation device to produce a product dialkyl carbonate stream and a water stream, thereby producing a product dialkyl carbonate stream.

11. The method claim 10, further comprising the step of combining a virgin alkanol stream with the alkanol tops stream and wherein in step (3) the virgin and the alkanol tops stream are contacted with oxygen and carbon monoxide in the presence of a catalyst to form the second dialkyl carbonate stream.

12. The method of claim 10, wherein distillation steps (2) and (4) are performed at overlapping times.

13. The method of claim 10, wherein:

the dialkyl carbonate comprises dimethylcarbonate, the alkanol comprises methanol, the diaryl carbonate comprises diphenyl carbonate, the aromatic alcohol comprises phenol, and the aromatic ether comprises anisole.

14. The method of claim 10, wherein the byproduct stream is introduced to the distillation column as a vapor.

15. The method of claim 10, wherein: the alkanol tops stream comprises greater than 60 wt % alkanol, less than 40 wt % dialkyl carbonate, and less than 10 ppm aromatic compound, and the first dialkyl carbonate bottoms stream comprises dialkyl carbonate, water, aromatic compound, and less than 1,000 ppm alkanol.

16. The method of claim 10, wherein the catalyst comprises CuCl, step (3) is performed in the presence of hydrochloric acid, and the second dialkyl carbonate stream further comprises oxygen, carbon monoxide, catalyst, and hydrochloric acid, wherein the method further comprises a step performed after step (3) and before step (4) of treating the second dialkyl carbonate stream to reduce the concentration of oxygen, carbon monoxide, catalyst, and hydrochloric acid.

* * * * *

UNITED STATES PATENT AND TRADEMARK OFFICE
CERTIFICATE OF CORRECTION

| | | |
|---|---|---|
| PATENT NO. | : 7,803,961 B2 | Page 1 of 1 |
| APPLICATION NO. | : 12/032385 | |
| DATED | : September 28, 2010 | |
| INVENTOR(S) | : Fernandez | |

It is certified that error appears in the above-identified patent and that said Letters Patent is hereby corrected as shown below:

Column 14, Claim 3, Line 29 should read as follows: -- The method of claim 2, further comprising the step of --

Column 14, Claim 5, Line 37 should read as follows: -- The method of claim 4, wherein steps (2) and (4) are performed --

Column 14, Claim 6, Lines 46 and 47 should read as follows: -- carbonate, water, aromatic compound, and less than 2,000 ppm alkanol. --

Column 15, Claim 11, Line 28 should read as follows: -- The method of claim 10, further comprising the step of --

Signed and Sealed this
Eleventh Day of January, 2011

David J. Kappos
*Director of the United States Patent and Trademark Office*